United States Patent [19]

Frick

[11] Patent Number: 4,907,601
[45] Date of Patent: Mar. 13, 1990

[54] ELECTROTHERAPY ARRANGEMENT

[75] Inventor: Kuno Frick, Balzers, Liechtenstein

[73] Assignee: Etama AG, Liechtenstein

[21] Appl. No.: 250,639

[22] Filed: Sep. 29, 1988

[30] Foreign Application Priority Data

Jun. 15, 1988 [EP] European Pat. Off. ........ 88109558.2

[51] Int. Cl.[4] .............................................. A61N 1/00
[52] U.S. Cl. ................................... 128/783; 128/421
[58] Field of Search ........... 128/791, 792, 793, 419 R, 128/783, 800, 801, 421, 422, 423 R; 340/407

[56] References Cited

U.S. PATENT DOCUMENTS

| 3,612,061 | 10/1971 | Collins et al. | 128/799 |
| 4,062,364 | 12/1977 | Masaki | 128/803 |
| 4,558,704 | 12/1985 | Petrofsky | 128/423 R |

FOREIGN PATENT DOCUMENTS

| 0029245 | 5/1981 | European Pat. Off. . | |
| 0145176 | 10/1984 | European Pat. Off. . | |
| 0268701 | 11/1986 | European Pat. Off. . | |
| 0257989 | 3/1988 | European Pat. Off. | 128/789 |
| 2437346 | 8/1974 | Fed. Rep. of Germany . | |
| 3437837 | 10/1984 | Fed. Rep. of Germany . | |

Primary Examiner—Lee S. Cohen
Assistant Examiner—Scott Getzow
Attorney, Agent, or Firm—Sughrue, Mion, Zinn, Macpeak & Seas

[57] ABSTRACT

An electrotherapy arrangement comprises a carrier centrally carrying an inner electrode portion constituting one voltage pole around which outer electrode portions constituting the other voltage pole concentrally lie, and means for applying voltage alternately to the outer portions, comprising a current source and a switching device, whereby the nature of the current and the switching procedures can be adjusted as desired.

25 Claims, 2 Drawing Sheets

ELECTROTHERAPY ARRANGEMENT

BACKGROUND OF THE INVENTION

The invention relates generally to an electrotherapy arrangement.

A wide variety of attempts have already been made, by means of electrical current, to treat physical ailments such as pains in the neck, headache, trigeminal neurolgia, facial neuralgia, Parkinson's disease, intervertebral disc injuries, torn discs, sports injuries and the like. For example German laid-open application (DE-OS) No. 34 37 837 describes an apparatus for the electrotherapeutic self-treatment of pain and sleeplessness, which comprises a plurality of electrodes of different metals and an auxiliary battery. Such apparatuses may possible produce temporary and short-term improvements in the ailments, but a reproducible and verifiable effect has not been demonstrated in practice.

In most cases it is in fact very difficult for the electrodes to reach those areas on the surface of the skin which are suitable for passing the current to those parts in the organism at which it is to produce its healing or pain-relieving effect. In addition, the currents which can be produced by different metals and batteries flow continuously so that it is not possible to produce any stimulus effects which usually always occur due to currents which vary in respect of time.

In addition there is a fear that certain areas of tissue may suffer from toxic loading as the battery is capable of dissolving the various metals in co-operation with physiological fluids such as for example perspiration, and the resulting metal ions can be transported into the organism.

U.S. patent specification No. 4 062 364 discloses a multi-pole electrode arrangement which is capable of supplying alternating current pulses. That arrangement has one positive and for example two negative electrodes which are always simultaneously supplied with ac voltage pulses. That electrode arrangement however is also not adequately suited to hitting points (for example electro-acupuncture points) which cannot be precisely located on the surface of the skin, so that frequently the pulses are to a certain extent useless by virtue of missing the target areas. As is known, current chooses the path of least resistance so that in addition it may frequently happen that only one of the negative electrodes actually results in a flow of current while the other negative electrode carries substantially no current, because of a higher degree of resistance at the surface of the skin at the location of that electrode. At any event that arrangement does not ensure that the supply of current is exact and precise.

Another form of electrotherapy arrangement includes an electrode plate comprising a treatment electrode which is subdivided into a plurality of portions, and a base electrode; voltage pulses are sent to the individual portions of the treatment electrode from a current source by way of a switching device at the same or different times in a specific or indeterminate sequence, those pulses then being able to go to the base electrode through a body disposed therebetween. That arrangement is intended inter alia to reach areas which lie deep in the organism, even if such areas cannot be precisely located, on the basis of a 'shotgun principle'. In that arrangement the base electrode is generally to be arranged at the side of the body which is opposite to the treatment electrode.

However the arrangements just discussed above do not afford the possibility of direct local treatment of individual points or locations on the surface of the skin.

Another form of electrode arrangement is referred to as an ear electrode, in which a saturated wad of cotton wool is placed in the ear canal; disposed around the ear muscles are actuatable contacts which also send pulses through the outer to the middle and inner ear on the basis of the 'shotgun principle'. With the simultaneous positioning and use of two devices (one each at the right ear and at the left ear), it was also possible to produce the same above-mentioned 'shotgun effect' in relation to areas lying in the interior of the head.

Mention may also be made of U.S. patent specification No. 4 558 704 disclosing an electrode arrangement which represents a substitute for numbed nerves in that current pulses are applied at given points on a body, such pulses stimulating the muscles therebeneath to perform activity. Systematic treatment of small limited areas on the basis of the above-mentioned 'shotgun principle' however cannot also be achieved with that arrangement.

SUMMARY OF THE INVENTION

An object of the present invention is to provide an electrotherapy arrangement which is easy to use and versatile in its mode of operation and effects.

Another object of the invention is to provide an electrotherapy arrangement which makes it possible to apply a physiologically effective form of current and amount of charge and which can be readily matched to the respective patient requirements.

Still another object of the present invention is to provide an electrotherapy arrangement capable of providing for direct stimulation of areas or locations at the surface of the skin of the body of a patient.

In accordance with the present invention, these and other objects are achieved by an electrotherapy arrangement comprising a current source, a switching means connected thereto and a multi-pole electrode means which is adapted to be connected to the switching device and which is disposed on a carrier. The electrode means comprises an inner pole or electrode portion, which is arranged substantially centrally on the carrier, and at least first, second and third outer poles or electrode portions arranged substantially in a circular configuration which is at least substantially concentric to the centre point of the inner electrode portion. The outer electrode portions can have voltage applied thereto with one polarity, by the switching means, alternately with a given frequency of switching-over between the electrode portions. The inner electrode portion carries the other polarity of the applied voltage. The voltage of the current source and the frequency of switching-over of the switching means are variable.

As will be seen in greater detail hereinafter in relation to specific embodiments, an electrotherapy arrangement according to the invention is simple to operate and the treatment (stimulation) is completely painless. In particular the individual setting of the frequency of switching over and/or the individual setting of the voltage make it possible to match the apparatus to the requirements of each respective patient. The currents applied to the organism by means of the electrotherapy arrangement are not experienced as unpleasant stimulus currents; however particularly strong, regulating and vitalising bio-energy is 'pumped' into the living organism by the currents used. The body is stimulated to heal by certain energy effects which cannot yet be entirely explained, and cell activity is stimulated, regulated and normalised. In that respect stimulation of the cells takes place with such a low current strength that the tissue being treated does not suffer any injuries such as for example current marks. The treated cells begin to function substantially better and initiate a healing process. That occurs in particular also in the case of cells whose location does not have to be precisely ascertained prior to the treatment being performed.

One explanation for the mode of operation of the arrangement according to the invention could be that the pulses which are introduced by the arrangement cause nerve stimuli to flow into the midbrain by way of quick-conducting A-nerve fibres. As on the other hand the pain stimuli are transported into the midbrain through slow-conducting C-nerve fibres, the pain can be suppressed. In the thalamus, one of the particularly important intermediate stations on the way to the cerebral cortex, which is the actual location of pain sensation, the fast nerve pulses block the slow pain pulses which thus do not reach the cerebral cortex or reach it only in an attenuated form . That theory which is referred to as the 'Gate control theory of pain' was put forward by Melzak and Wal in Canada, and has been supplemented and confirmed on many occasions.

Besides that theory, natural substances were also already found in 1975 which (similarly to morphine) have a strongly analgesic effect, known as 'endorphines'. Such endorphines are liberated by the action of the arrangement according to the invention and produce an additional painrelieving effect.

In accordance with a preferred feature of the invention the outer poles or electrode portions have voltage applied thereto of negative polarity relative to the inner pole or electrode portion, as it has been found that in various forms of therapy it is advantageous to use the specified polarity. In that arrangement, switching over from an outer pole to the respectively adjacent pole gives rise to the occurrence, at the individual poles which are respectively actuated, of brief dc voltage values which can also be referred to as rectangular pulses. With the specified polarity, it is assumed that that is beneficial to the direction of transportation of nerve pulses and/or the liberation of endorphines.

The direction of progression in regard to the delivery of pulses, or the application of voltage to the individual outer electrode portions, is preset in accordance with the nature of the tissue to be treated. There is not yet a clear explanation for that mode of operation, but various tests have demonstrated that the direction of progression is frequently an aspect of significance. In cases in which the appropriate direction of progression cannot be clearly established at the beginning of the treatment, automatic reversal of the direction of rotation can usefully be adapted.

As was empirically ascertained, the level of the frequency of switching over is often also a matter of importance in regard to the healing action, even if there is still no clear explanation therefor. It is assumed that this depends on the general physiological state of the parts of the body in question as that state can either accelerate or retard the liberation of endorphines. Adaptation to such acceleration and retardation can now be effected by varying the frequency of switching over in the arrangement according to the invention.

It was found that in many cases geometrical dissimilarity of the inner pole and the outer poles is advantageous, while a spacing of about 2 cm between the inner pole or electrode portion and each of the outer ones was found to be that giving the highest level of efficiency with at the same time the best certainty of aim.

The use of electrodes of gold or gold alloy prevents certain areas of tissue from being poisoned by migrating metal ions, it improves the possibility of keeping the electrode clinically clean and it reduces the danger of irritations as may occur for example due to the use of silver. The poles or electrode portions may additionally or alternatively be curved convexly away from the carrier, the curved configuration ensuring optimum transfer of current to the skin even at parts of the body which are covered with hair.

The poles or electrode portions may be connected to a cable connecting to the switching device by means of for example printed conductor tracks which are integrated in the carrier, to increase the speed of assembly for the electrode. The carrier may be transparent, for example of acrylic glass. Transparency of the carrier permits reliable positioning of the electrode at certain parts of the skin. A doctor may for example mark with a pen an electro-acupuncture point which he has previously found by using electronic measuring equipment, and may apply the electrode to that point with the utmost accuracy as he can view the marked point through the transparent carrier.

When simultaneously treating different locations, for example acupuncture points for left and right ovaries of a female patient, it is advantageous for the switching device to be designed for the connection of a plurality of electrodes. Experience has shown that points which are different in terms of symmetry on a patient require the same form of current so that a single current source is sufficient.

The arrangement may advantageously provide for a random or automatic variation in the current values, which helps to apply the correct current shape if precise analysis prior to the treatment operation was not possible. Experience shows that the other current shapes which are not accurate harmlessly produce no effect, presumably due to lack of strength.

The arrangement may also include a measuring device or an oscilloscope for reading off the values involved in operation of the arrangement, which may be a matter of importance on the one hand from the point of view of the doctor performing the treatment or in regard to the therapy record thereof, while on the other hand the patient can also recognise that certain pulses are applied to his body in a particular way, which can provide mental stimulation for him in the healing process.

The optimum switching-over frequency values used in the electrotherapy arrangement occur in the range of from 0.5 to 20 Hertz; in the simplest case, due to an automatic variation in the frequency of switching over, they result in a high degree of accuracy and success with the therapy, while, although the currents in the physiological field, in a range of values of from about 1 to 1000 microamps, can only be measured with difficulty, they are however highly effective from the therapeutic point of view.

With the nature of the surface of the skin and the conductivity thereof, as usually found on the human body, in order to produce the desired currents it is preferred that the current source can be set in the voltage range of from about 1.2 to 7 V. Voltage values of from 1.7 to 1.8 V are preferred.

In a preferred feature of the invention the switching device and the power source are jointly disposed in a casing, thus affording ease of transportability and a compact construction, more particularly in a fully transistorised version.

DESCRIPTION OF THE PREFERRED EMBODIMENTS

Figure 1:
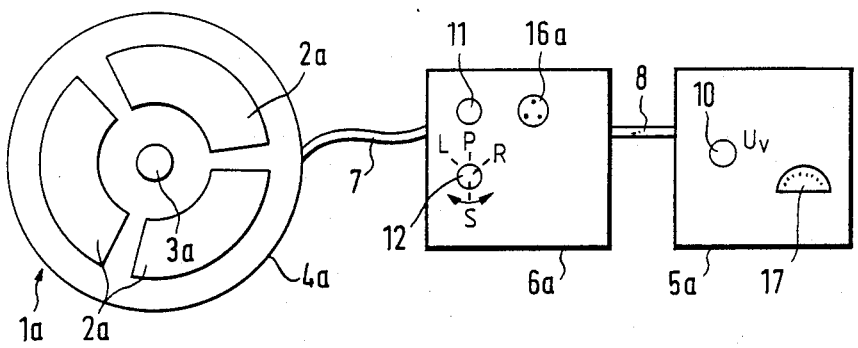
FIG. 1 shows a first embodiment of the arrangement of the invention with an outer electrode comprising outer electrode portions in the form of segments of a circular ring.

In the drawing the same components are denoted by the same reference numerals while similar components are denoted by the same reference numerals but with different letter indices. The Figures are first described generally to provide an overview of the arrangement according to the invention.

Figure 2:
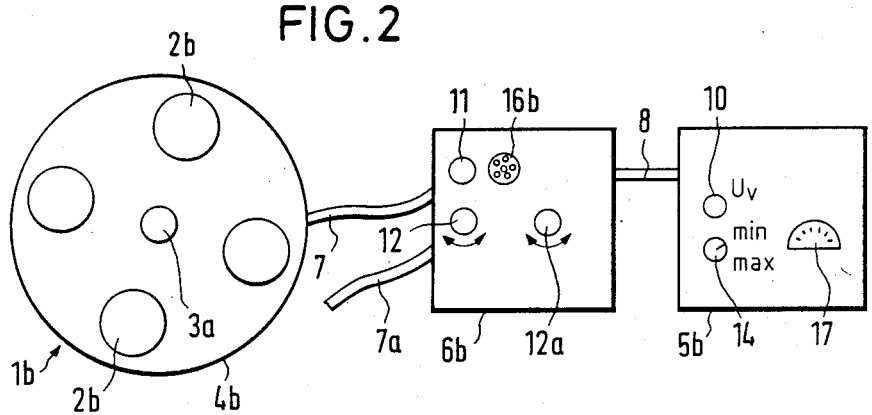
FIG. 2 shows a second embodiment of the arrangement of the invention with an outer electrode having four circular outer poles or electrode portions.
Figure 3:
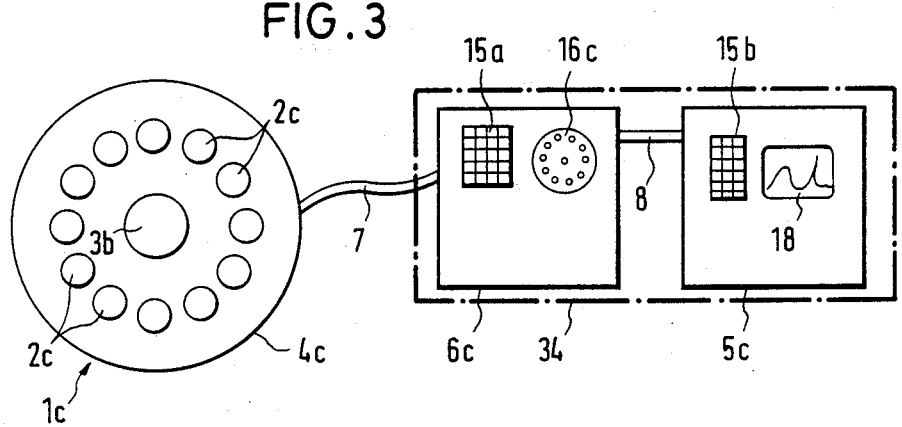
FIG. 3 shows a third embodiment of the arrangement of the invention with an electrode array in which twelve outer circular poles are disposed around an inner pole or electrode portion on a circle which is concentric with respect to the centre point of the inner pole.

Referring firstly to FIGS. 1 through 3, the arrangement has a plurality of electrodes of different configurations for correspondingly different uses. The electrode array 1a in FIG. 1 has only three outer electrode portions or poles 2a which are in the form of sectors of a circular ring and which are arranged substantially concentrically around an inner pole or electrode portion 3a disposed centrally on a carrier 4a. They cover a large area of the region of the body which is to be treated, while the actual transfer of current takes place, in dependence on the locally variable conductivity of the surface of the skin, only at individual regions of the poles 2a, 3a.

The arrangements shown by way of example in FIGS. 2 and 3 differ from the FIG. 1 arrangement, the arrangement in FIG. 2 having four outer poles 2b and the arrangement shown in FIG. 3 having twelve outer poles 2c.

All the poles 2a, 2b, 2c and 3a, 3b 3c are respectively mounted on carrier 4a, 4b, 4c which is transparent for better locating the region of the body which is to be treated. The carrier is preferably made from acrylic glass, while the poles comprise metal sheet, for example gold sheet or a sheet of gold alloy, and are fixed on a surface of the carrier 4a, 4b, 4c. They are preferably curved convexly away from the carrier 4. The electrical feed to the individual poles is by way of conductor tracks in the manner of a printed circuit (not shown in the drawing), preferably integrated with the carrier 4a, 4b, 4c. The electrodes in each illustrated arrangement are connected to a switching device 6a, 6b, 6c by way of a multi-wire connecting cable 7, while the switching device is in turn connected to a power source 5a, 5b, and 5c respectively by a further cable 8.

The switching device 6a shown in FIG. 1 has a rotary knob 11 for setting the frequency of switching over the supply of current successively to the electrode portions 2a, and also an LED-display 16a which is connected in parallel with the poles 2a and which shows the respective condition of actuation of the poles 2a. That means that an LED (light emitting diode) of the display 16a is lit whenever an outer pole of the electrode array 1a, which is connected thereto, has voltage applied thereto. The arrangement of FIG. 1 also has a rotary knob 12 for selecting the desired direction of progression of supplying power to the outer poles 2a. In position L, the direction of progression is in the counter-clockwise direction in FIG. 1, in position R it is in the clockwise direction and in position P there is no progression at all, but on the contrary all the outer poles 2a have voltage applied thereto simultaneously. In that last-mentioned switching condition, the current finds its own way, in dependence on the locally different conductivity of the skin in the area in question. Furthermore the rotary knob 12 has a position S in which the direction of progression is automatically reversed after having run through the individual poles 2a.

In FIG. 2 the switching device 6b has a double cable 7, 7a so that two 1b of which only one is shown in FIG. 2 and which are the same as each other can be operated simultaneously. In the FIG. 2 construction the electrode arrays 1b each include four outer poles 2b which are uniformly distributed on a circle which is concentric with respect to the centre point of the inner pole 3a.

The switching device 6c shown in FIG. 3 has a programmable computer with a program input panel 15a for randomly determining the respective switching sequence in which the outer poles 2c of the electrode array 1c are operated with current.

In all the embodiments illustrated the switching device 6a, 6b, 6c is connected in each case to the current source 5a, 5b, 5c by way of a line 8. As can be seen from FIG. 3, the switching device 6c and the current source 5c are preferably integrated in their own joint casing 34.

The current source 5a of the first embodiment shown in FIG. 1, in its simplest design, has a rotary knob 10 of setting the voltage Uv supplied to the electrode array 1a and a measuring device 17 for indicating the respectively set voltage values.

The current source 5b shown in FIG. 2, besides the knob 10 also has a rotary knob 14 for minimum and maximum setting of the voltage Uv.

The current source 5c shown in FIG. 3 is programmable completely and in respect of all relevant parameters by way of the program input panel 15b. An oscilloscope 18 shows the electrical parameters which are produced by virtue of the programming.

Figure 4:
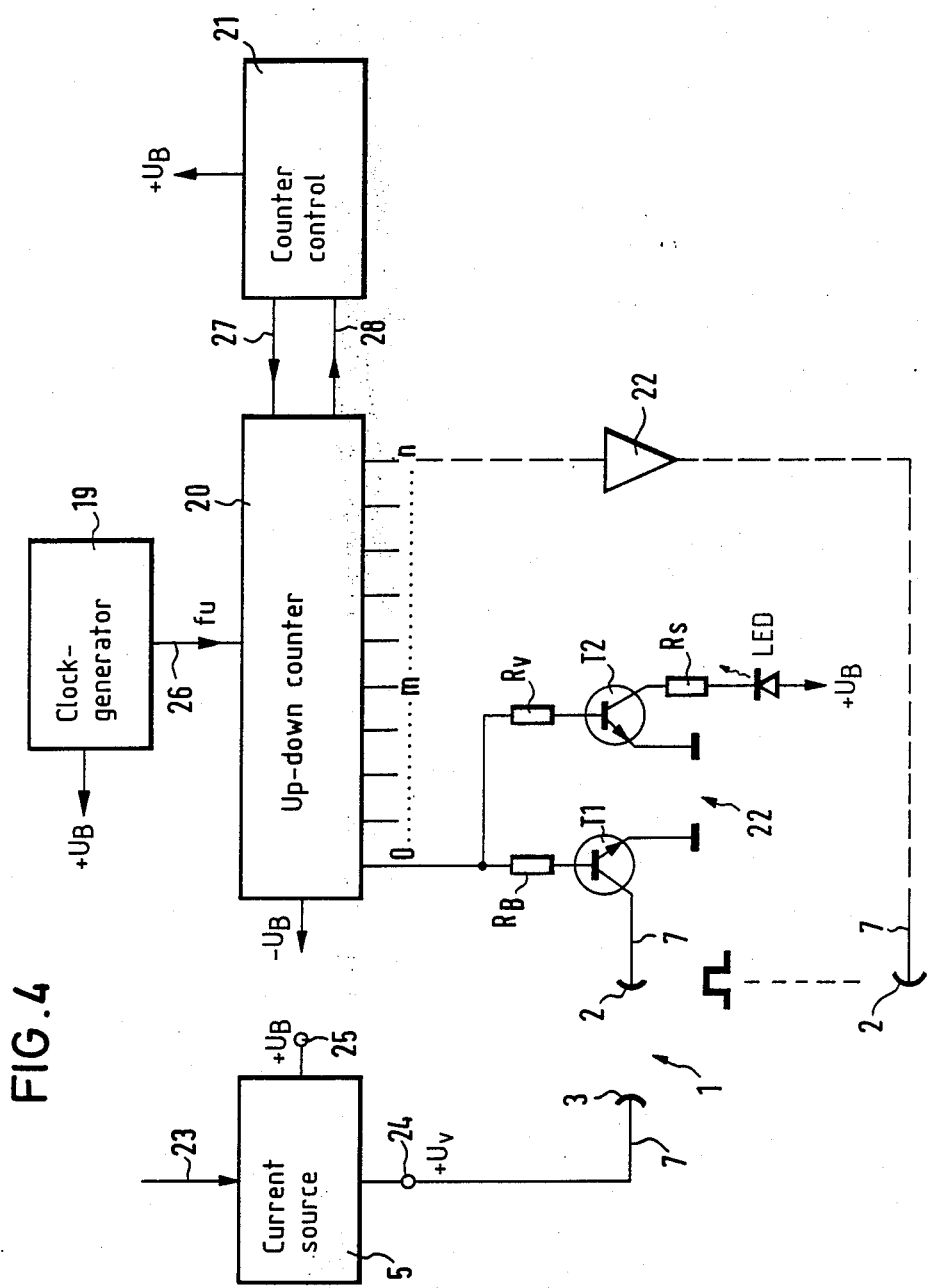
FIG. 4 shows a schematic block diagram of a unit consisting of the current source and the switching device.

Reference will now be made to FIG. 4 showing a block circuit diagram of the assembly of an electrode array indicated generally at 1, a current source 5 and the switching or control device 6.

The device 6 includes a clock generator 19, an up-down counter 20, a counter control 21 and a plurality of driver arrangements 22 for each output of the counter 20. The outputs of the driver circuits 22 are each connected by way of the wires of the cable 7 to a respective one of the outer poles 2 of the electrode array 1.

The current source 5 is constructed in a manner with which the man skilled in the art is familiar. It includes a voltage source for the constant operating voltage $U_B$ of the electronic components of the switching device 6. That constant operating voltage $U_B$ is outputted at the output 25 of the current source. The current source 5 also includes a second voltage source whose output voltage Uv is adjustably variable and is outputted at the output 24 of the current source 5. The range of adjustment of the variable voltage $U_v$ is from about 1.2 V to 7.0 V. The value Uv is preferably set at 1.7 V to 1.8 V.

As illustrated, the output 24 of the current source 5 is directly connected to the inner pole 3 of the electrode array 1 by way of a wire of the cable 7 for supplying the positive polarity of Uv. The output 25 is connected to the respective current supply connections of the individual components of the switching device 6 for the feed of the positive operating voltage $U_B$. That is only indicated in the block circuit diagram, the individual supply lines being omitted in order to make the drawing easier to read. The supply of power for the current source 5 is by way of an input 23 from a current mains or alternatively from a battery.

The clock generator 19 of the switching device 6 is also of conventional construction. At its output 26 the clock generator 19 produces rectangular pulses with a repetition frequency fu which are supplied to the counting input of the counter 20. The frequency produced by the clock generator 19 may be set in a range of from about 0.5 to 20 Hertz.

The counter 20 is in the form of an up-down counter with n outputs. The number n of outputs is at least as high as the number of outer poles 3 to be operated in the electrode array 1 used.

Upon being actuated by the clock generator 19, the counter 20 counts the supplied number of clock pulses in such a way that a signal appears at respective ones of its outputs 0 to n. The direction of counting of the counter 20 can be influenced by way of the line 27 in such a way that the counter 20 either counts from the output 0 by way of the output m in a rising sequence to the last output n, or in the reverse sequence. It is also possible for the counter 20 to be controlled by way of the line 27 in such a way that it initially counts from the output 0 to a selectable output m, then reverses its direction of counting and counts back to the output 0, where it again reverses its direction for counting, and so forth.

For the purposes of controlling the desired mode of counting, the circuitry includes the counter control 21 which, by way of the line 28, detects the count condition of the counter which has just been reached, that is to say the output m which has just been supplied with a signal, and then, depending on its respective setting, by way of the line 27, produces the command either to continue counting up to a further predeterminable output, for example the last output n, and then to count in the down direction, or to do that upon reaching a middle output m. It is also possible to set the counter control 21 in such a way that a counting sequence of 0 to n is always observed, always beginning again at 0. The design configuration of such a counter control is not a central component of the invention and is known to the man skilled in the electronics acts.

Each of the individual outputs 0 to n of the counter operates a driver arrangement 22 The drawing only shows in detail the driver arrangement for the output 0, while it also shows that for the last output n, in symbolic form. The driver arrangements 22 which are associated with the intermediate outputs of the counter 20 and which are of entirely the same configuration are omitted for the sake of clarity.

As shown in detail in respect of the output 0, each driver arrangement 22 includes two driver circuits. One driver circuit includes a transistor T1 which is controlled by way of a base resistor $R_B$; the emitter of the transistor T1 is connected to ground and the collector thereof is connected by way of a wire of the cable 7 to an outer pole 2 of an electrode array 1. When the counter 20 has reached the count value 0 and therefore a signal occurs at its output 0, the transistor T1 is switched on so that the outer pole 2 connected thereto is grounded by way of the cable 7 and therefore for example the voltage +Uv obtains between the inner pole 3 and the outer pole 2. Provided in parallel with that first driver at the output 0 within the driver arrangement 22 is a second driver comprising a series resistor Rv and the transistor T2. The transistor T2 is controlled by way of the series resistor Rv at its base. Its emitter is connected to ground while its collector is connected by way of a protective resistor to a light emitting diode LED of the LED-display 16. The light emitting diode LED is connected with one electrode to the fixed operating voltage $+U_B$. When therefore the counter 20 reaches the count value 0 and thus a signal occurs at its output 0, the transistor T2 is also switched on, and the light emitting diode LED connected thereto is supplied with current and is lit. In that way the LED-display indicates which outer pole of the electrode array 1 is just being operated, and how the progression of the voltage at the outer poles is taking place.

It will be appreciated that the above-described embodiments of the arrangement according to the invention have been set forth solely by way of example and illustration of the invention and that various other modifications and alterations may be made therein without departing from the scope of the invention.

What is claimed is:

1. An electrotherapy arrangement comprising: a current source; a switching means connected thereto; a carrier bearing an electrode array adapted to be connected to the switching means, the electrode array including at least first, second and third outer electrode portions constituting a pole of the array and arranged substantially in a circle and an inner electrode portion constituting the other pole of the electrode array and arranged substantially at the center of the circle, the switching means being operable to apply voltage to the outer electrode portions with one polarity alternately with a given frequency of switching-over from one said electrode portion to another while the inner electrode portion carries the other polarity; and means for varying the voltage of the current source and the switching-over frequency of the switching means.

2. An arrangement as set forth in claim 1 wherein said switching means is adapted to apply voltage of negative polarity to the outer electrode portions, relative to the inner electrode portion.

3. An arrangement as set forth in claim 1 wherein said switching means is adapted to apply voltage to the outer electrode portions in succession selectively in the clockwise and counter-clockwise directions.

4. An arrangement as set forth in claim 1 wherein said switching means is adapted to apply voltage to the outer electrode portions, in such a way that the sequence of applying voltage to the outer electrode portions is automatically reversed when a specified outer electrode portion is reached.

5. An arrangement as set forth in claim 1 including means for adjusting the switching-over frequency in accordance with a predetermined program.

6. An arrangement as set forth in claim 1 and including a display means for the switching operation.

7. An arrangement as set forth in claim 6 wherein said display means is an LED-display.

8. An arrangement as set forth in claim 1 wherein the outer and inner electrode portions are of different surface measurements.

9. An arrangement as set forth in claim 8 wherein the spacing between the inner and the outer electrode portions is about 2 cm.

10. An arrangement as set forth in claim 1 wherein the electrode portions substantially comprise gold.

11. An arrangement as set forth in claim 1 wherein the electrode portions substantially comprise gold alloy.

12. An arrangement as set forth in claim 1 wherein the electrode portions are curved convexly away from the carrier.

13. An arrangement, as set forth in claim 1, further comprising a connecting cable electrically interconnecting said electrode portions and said switching means, and wherein the electrode portions are connected to said connecting cable via electrical conductor tracks integrated in the carrier.

14. An arrangement as set forth in claim 13 wherein the conductor tracks are printed.

15. An arrangement as set forth in claim 1 wherein the carrier is made from transparent plastic material.

16. An arrangement as set forth in claim 15 wherein said plastic material is acrylic glass.

17. An arrangement, as set forth in claim 1, further comprising means (7a) for connecting the switching means to another said electrode array.

18. An arrangement as set forth in claim 1 including means for automatically altering the variation in the voltage of the current source and the switching-over frequency of the switching means in accordance with a program.

19. An arrangement as set forth in claim 1 including means for adjusting at least the minimum and maximum voltage values of the current source and a means for reading off the respective values.

20. An arrangement as set forth in claim 19 wherein said reading-off means comprises a measuring device.

21. An arrangement as set forth in claim 19 wherein said reading-off means comprises an oscilloscope.

22. An arrangement as set forth in claim 1 wherein said switching-over frequency of the switching means is variable between 0.5 and 20 Hertz and the current strength produced by the current source is in the range of from 1 to 1000 $\mu$A.

23. An arrangement as set forth in claim 1 wherein the voltage of the current source is adjustable in a range of from about 1.2 V to 7.0 V.

24. An arrangement as set forth in claim 1 including a casing in which the switching means and the current source are disposed jointly.

25. An arrangement as set forth in claim 1, wherein the voltage of the current source is adjustable from 1.7 V to 1.8 V.

* * * * *